(12) United States Patent
Yuksel et al.

(10) Patent No.: US 7,896,920 B2
(45) Date of Patent: *Mar. 1, 2011

(54) IN SITU BIOPROSTHETIC FILLER AND METHOD, PARTICULARLY FOR THE IN SITU FORMATION OF VERTEBRAL DISC BIOPROSTHETICS

(75) Inventors: K. Umit Yuksel, Kennesaw, GA (US); Steven P. Walsh, Marietta, GA (US); Kirby S. Black, Achworth, GA (US)

(73) Assignee: CryoLife, Inc., Kennesaw, GA (US)

( * ) Notice: Subject to any disclaimer, the term of this patent is extended or adjusted under 35 U.S.C. 154(b) by 144 days.

This patent is subject to a terminal disclaimer.

(21) Appl. No.: 11/932,066

(22) Filed: Oct. 31, 2007

(65) Prior Publication Data

US 2008/0058942 A1 Mar. 6, 2008

Related U.S. Application Data

(63) Continuation of application No. 09/983,537, filed on Oct. 24, 2001.

(60) Provisional application No. 60/242,457, filed on Oct. 24, 2000.

(51) Int. Cl.
*A61F 2/44* (2006.01)
*A61B 17/68* (2006.01)
(52) U.S. Cl. .................. 623/17.16; 623/17.11; 606/86 A
(58) Field of Classification Search ..................... 606/93, 606/92, 94, 90, 86 A; 623/17.11–17.16
See application file for complete search history.

(56) References Cited

U.S. PATENT DOCUMENTS

| 4,309,777 A | 1/1982 | Patil |
| 4,394,370 A | 7/1983 | Jefferies |
| 4,472,840 A | 9/1984 | Jefferies |
| 4,620,327 A | 11/1986 | Caplan et al. |

(Continued)

FOREIGN PATENT DOCUMENTS

EP 0968729 A2 1/2000

(Continued)

OTHER PUBLICATIONS

Japanese Office Action mailed Dec. 11, 2007 with English Translation (5 pages total) corresponding to Japanese Patent Application Serial No. 2002-537171.

(Continued)

*Primary Examiner* — Pedro Philogene
(74) *Attorney, Agent, or Firm* — Sutherland Asbill & Brennan LLP

(57) ABSTRACT

Bioprosthetic devices include an exterior biological tissue member which at least partly defines a cavity, and a proteinaceous biopolymer which fills the cavity, and intercalates and is chemically bound (fixed) to the tissue of the surrounding biological tissue member. In preferred forms, the bioprosthetic device is a bioprosthetic vertebral disc having a fibrillar outer annulus which surrounds and defines an interior cavity and is formed by removal of at least a substantial portion of the natural gelatinous core therefrom. The cavity defined by the fibrillar outer annulus may then be filled with a flowable proteinaceous biopolymer. Preferably, the proteinaceous biopolymer is a liquid mixture comprised of human or animal-derived protein material and a di- or polyaldehyde, which are allowed to react in situ to form a cross-linked biopolymer within the cavity. The liquid mixture may be formed in advance of being introduced into the cavity, or may be formed simultaneously during introduction into the cavity.

24 Claims, 1 Drawing Sheet

U.S. PATENT DOCUMENTS

Figure 1:
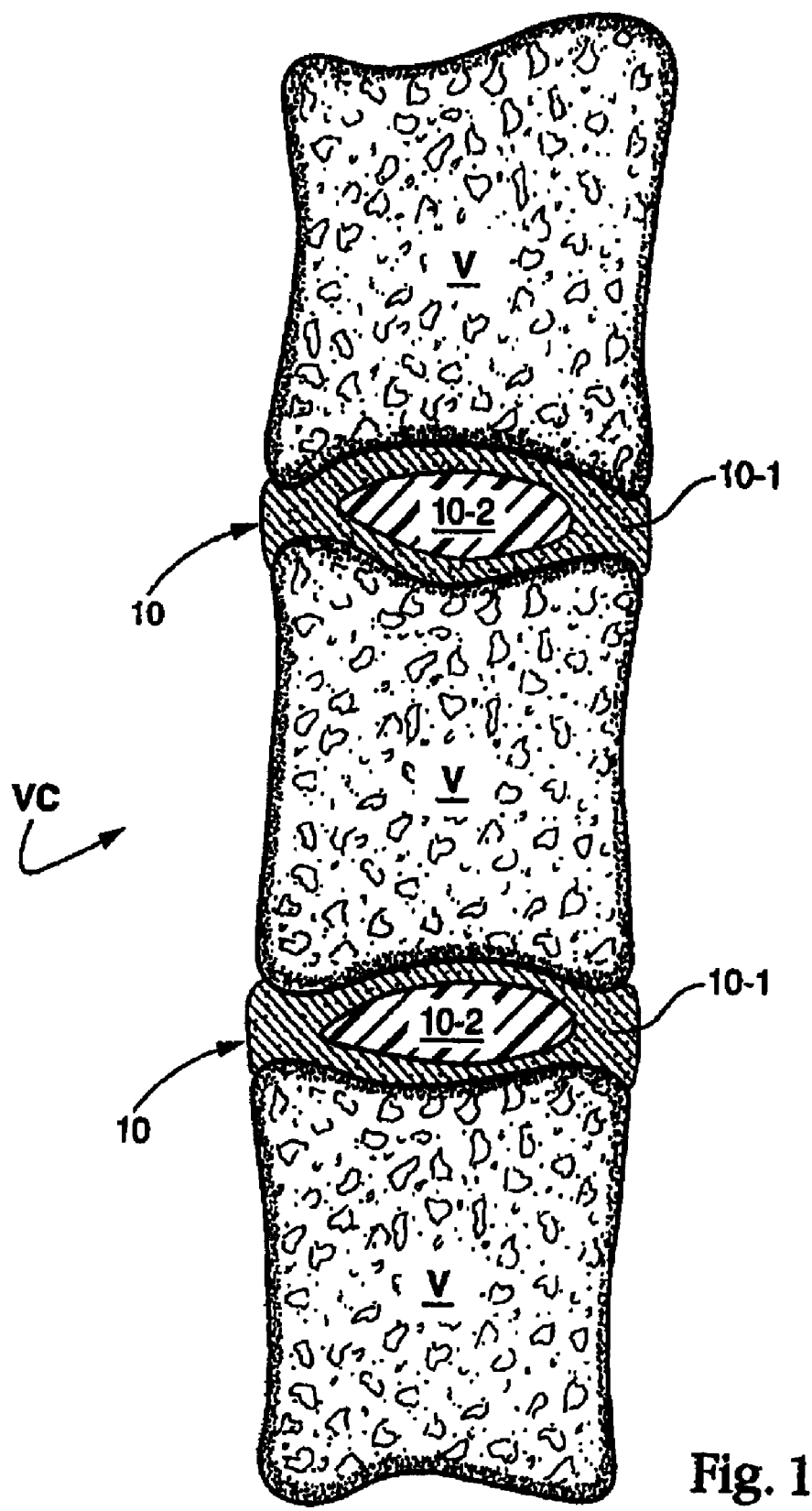

| | | | |
|---|---|---|---|
| 4,623,553 A | 11/1986 | Ries et al. | |
| 4,655,980 A | 4/1987 | Chu | |
| 4,714,469 A | 12/1987 | Kenna | |
| 4,759,766 A | 7/1988 | Buettner-Janz et al. | |
| 4,911,718 A | 3/1990 | Lee et al. | |
| 5,071,437 A | 12/1991 | Steffee | |
| 5,099,003 A | 3/1992 | Kotitschke et al. | |
| 5,213,580 A | 5/1993 | Slepian et al. | |
| 5,258,028 A | 11/1993 | Ersek et al. | |
| 5,373,431 A | 12/1994 | Hayman et al. | |
| 5,385,606 A * | 1/1995 | Kowanko | 106/156.3 |
| 5,510,418 A | 4/1996 | Rhee et al. | |
| 5,514,180 A | 5/1996 | Heggeness et al. | |
| 5,606,019 A | 2/1997 | Cappello | |
| 5,755,797 A | 5/1998 | Baumgartner | |
| 5,766,584 A | 6/1998 | Edelman et al. | |
| 5,800,549 A * | 9/1998 | Bao et al. | 606/99 |
| 5,817,303 A | 10/1998 | Stedronsky et al. | |
| 5,824,093 A | 10/1998 | Ray et al. | |
| 5,827,328 A | 10/1998 | Buttermann | |
| 5,865,845 A | 2/1999 | Thalgott | |
| 5,865,846 A | 2/1999 | Bryan et al. | |
| 5,874,500 A | 2/1999 | Rhee et al. | |
| 5,900,245 A | 5/1999 | Sawhney et al. | |
| 5,906,997 A | 5/1999 | Schwartz et al. | |
| 6,018,030 A | 1/2000 | Ferrari et al. | |
| 6,045,580 A | 4/2000 | Scarborough et al. | |
| 6,048,346 A * | 4/2000 | Reiley et al. | 606/92 |
| 6,051,648 A | 4/2000 | Rhee et al. | |
| 6,066,325 A | 5/2000 | Wallace et al. | |
| 6,099,565 A | 8/2000 | Sakura, Jr. | |
| 6,140,452 A * | 10/2000 | Felt et al. | 528/60 |
| 6,166,130 A | 12/2000 | Rhee et al. | |
| 6,183,581 B1 | 2/2001 | Ducci et al. | |
| 6,206,921 B1 * | 3/2001 | Guagliano et al. | 606/92 |
| 6,264,659 B1 | 7/2001 | Ross et al. | |
| 6,264,695 B1 | 7/2001 | Stoy | |
| 6,332,894 B1 | 12/2001 | Stalcup et al. | |
| 6,395,032 B1 | 5/2002 | Gauchet | |
| 6,436,143 B1 * | 8/2002 | Ross et al. | 623/17.16 |
| 6,482,235 B1 | 11/2002 | Lambrecht et al. | |
| 6,488,952 B1 | 12/2002 | Kennedy et al. | |
| 6,723,335 B1 | 4/2004 | Moehlenbruck et al. | |
| 6,805,697 B1 | 10/2004 | Helm et al. | |
| 6,921,412 B1 | 7/2005 | Black et al. | |
| 6,936,070 B1 * | 8/2005 | Muhanna | 623/17.12 |
| 6,994,686 B2 | 2/2006 | Cruise et al. | |
| 7,004,945 B2 | 2/2006 | Boyd et al. | |
| 7,183,369 B1 | 2/2007 | Mallapragada et al. | |
| 7,621,959 B2 * | 11/2009 | Yuksel et al. | 623/17.16 |
| 2004/0091540 A1 | 5/2004 | Desrosiers et al. | |
| 2004/0220296 A1 | 11/2004 | Lowman et al. | |
| 2006/0089721 A1 | 4/2006 | Muhanna et al. | |
| 2007/0173943 A1 | 7/2007 | Dulak et al. | |

FOREIGN PATENT DOCUMENTS

| | | |
|---|---|---|
| JP | 3-127709 | 5/1991 |
| WO | WO 89/04646 | 6/1989 |
| WO | 00/45870 | 8/2000 |
| WO | 00/47245 | 8/2000 |
| WO | 0062832 | 10/2000 |

OTHER PUBLICATIONS

Office Action mailed Jun. 24, 2008 corresponding to U.S. Appl. No. 11/008,609.

* cited by examiner

IN SITU BIOPROSTHETIC FILLER AND METHOD, PARTICULARLY FOR THE IN SITU FORMATION OF VERTEBRAL DISC BIOPROSTHETICS

CROSS-REFERENCE TO RELATED APPLICATION APPLICATIONS

The present application is a continuation application of U.S. patent application Ser. No. 09/983,537 filed Oct. 24, 2001, which is based on, and claims domestic priority benefits under 35 USC §119(e) from U.S. Provisional Application Ser. No. 60/242,457 filed Oct. 24, 2000, each of which the entire content thereof is expressly incorporated herein by reference.

FIELD OF THE INVENTION

The present invention relates generally to bioprosthetics. In especially preferred embodiments, the present invention is related to bioprosthetics formed in situ.

BACKGROUND AND SUMMARY OF THE INVENTION

The vertebral disc is a collagenous spacer positioned between the vertebral bones of the spinal column. The disc generically consists of a tough fibrillar outer annulus (annulus fibrosus) and a highly hydrated gelatinous core (nucleus pulposus). The vertebral disc serves as a shock absorber to dissipate the energy of impact loading on the back, as well as a joint, allowing flexion and extension of the human torso.

Degeneration of vertebral disc function in the lumbar portion of the spine is the leading cause of debilitating low back pain in adults over the age of 35. Degenerative disc disease (DDD) is characterized by a gradual collapse of the vertebral disc due to dehydration of the nucleus pulposus, or by a bulging of the annulus fibrosus. DDD may also precipitate the formation of fissures within the annulus that allows extrusion of the disc nucleus (disc herniation) resulting in a sudden collapse in the disc height and the potential for nerve root and/or spinal cord compression. Disc herniation may also result due to trauma related over compression of the spine, such as a heavy sitting fall.

Chronic diffuse low back pain results from irritation of pain receptors in the outer third of the disc annulus and surrounding soft tissues as the disc collapses. Radicular pain results from direct compression of the affected nerve root by extruded or bulging disc tissue. Aggressive and extensive physical therapy and drug treatments are the first line treatments for debilitating back pain. In the absence of acceptable pain resolution, surgical intervention is indicated.

The traditional surgical procedures for treatment of intractable low back pain due to DDD call for either fusion of the vertebral bodies above and below the affected disc, or removal of the nuclear material thorough open surgical, micro-surgical or endoscopic procedures. Recently, novel procedures involving thermal shrinkage of the collagenous lamina with an electrothermal catheter or laser device have been applied. The removal of the nucleus leaves a void within the disc, and eliminates the viscoelastic fluid that acts as a shock absorber. This void and absence of the viscoelastic fluid creates an opportunity for the lamina to collapse inward and allows the disc space to collapse further. The collapse of the disc space can lead to loss of motion and morbidity, as during the collapse of the disc space the nerves radiating from the spinal column may be pinched.

Many surgical techniques and specialized devices have been generated to combat the problem of progressive disc collapse resulting from disc denucleation. Harvested autologous bone has been placed within the denucleated disc space to afford a bony bridge or fusion between the two vertebral bodies. Pedicle screws and other spinal instruments, such as rods and plates, are mechanically affixed to the vertebral bodies, stabilizing the vertebra and preventing further collapse. The problem with these, and other fusion techniques, is the prevention of motion at the level of repair, and resultant transfer of stresses to the levels above and below. These additional loading stresses inevitably result in the degeneration of these disc levels as well.

The patent literature discloses several apparati for the replacement of an entire disc (i.e., prosthetic vertebral disc), whereby the damaged disc is removed and a device is anchored to the vertebral bone below and above the damaged disc. The ultimate goal of such a design concept is to maintain or regain the mobility of the native vertebra-disc-vertebra motion segment. Varying degrees of mobility have been claimed for different types of mechanical disc replacements. The following is a non-exhaustive list of such U.S. Patent disclosures;[1] U.S. Pat. No. 4,309,777 to Patil; U.S. Pat. No. 5,865,845 to Thalgott; U.S. Pat. No. 5,827,328 to Buttermann; U.S. Pat. No. 5,865,846 to Bryan et al; U.S. Pat. No. 4,759,766 to Buettner-Jantz et al.; U.S. Pat. No. 5,071,437 to Steffe; U.S. Pat. No. 4,911,718 to Lee at al.; and U.S. Pat. No. 4,714,469 to Kenna. The utility of these prior design proposals has been principally limited by an inability to adequately anchor the flexible prosthetic disc to the bony vertebra.

[1] The entire disclosure of each U.S. Patent cited hereinafter is hereby expressly incorporated hereinto by reference.

An alternate approach to the repair of damaged or diseased vertebral discs is to physically prevent disc collapse through the insertion of a rigid body into the disc space. The insertion of tubular or other hollow devices, that may, in addition, contain openings through their walls to allow bone growth through the device, enable the motion segment to be fused with the vertebral spacing maintained. These open or tubular devices may be constructed of metallic alloys traditional to implantable medical devices (e.g., stainless steel, titanium and titanium alloys), carbon fiber reinforced engineering thermoplastics (e.g., polyetheretherketones), or machined human cortical bone. These devices have been disclosed, for example, in U.S. Pat. No. 4,961,740 to Ray et al; U.S. Pat. No. 5,015,247 to Michelson; U.S. Pat. No. 5,766,253 to Brosnahan; U.S. Pat. No. 5,425,772 to Brantigan; and U.S. Pat. No. 5,814,084 to Grivas et al. While these devices may retain the proper spacing between the vertebra (i.e., the disc height), they are disadvantageous since, as the two vertebrae are fused, motion across the vertebra-disc-vertebra element is eliminated.

Another general technique for the preservation of vertebral body separation is to replace the removed disc nuclear tissue with non-fusing, non-rigid materials. One prior proposal suggests using a bladder that can be filled with liquid to restore disc height (see, U.S. Pat. No. 3,875,595 to Froning). One other prior proposal is disclosed in U.S. Pat. No. 5,534,028 to Bao et al, where a pre-cast pre-shaped hydrogel in placed into the void. Variations on the type of device disclosed in Bao et al '028 are likewise disclosed in U.S. Pat. Nos. 5,976,186, 5,192,326, and 5,047,055. Preformed inserts made from a xerogel plastic as a nucleus pulposus replacement have also been disclosed in U.S. Pat. No. 6,264,695. A cylindrical hydrogel pillow that is contained within a non-expanding casing and assorted variations thereof are described in U.S. Pat. Nos. 4,772,287, 4,904,260, 5,674,295, 5,824,093, and 6,022,376. In this regard, the device shown in U.S. Pat. No. 6,022,376 is inserted into tunnels drilled into the disc as a dehydrated hydrogel resin, and is allowed to rehydrate and swell once it is inserted. The swelling holds the device in place while preventing the collapse of the denucleated disc. However, the device is neither chemically nor mechanically fixated in place.

It has also been disclosed in U.S. Pat. Nos. 6,183,581, 6,206,921 and 6,264,659, that molten gutta percha and its compounds may be used as possible replacements of nucleus pulposus.

Broadly, the present invention relates to bioprosthetic devices comprised of an exterior biological tissue member which at least partly defines a cavity, and a proteinaceous biopolymer which fills the cavity, and intercalates is chemically bound (linked) to the surrounding biological tissue member. In preferred forms, the bioprosthetic device is a bioprosthetic vertebral disc having a fibrillar outer annulus which surrounds and defines an interior cavity and is formed by removal of at least a substantial portion of the natural gelatinous core therefrom. The cavity defined by the fibrillar outer annulus may then be filled with a flowable biopolymeric material which is then allowed to at least partly solidify in situ (e.g., most preferably by in situ cross-linkage reaction) to form a proteinaceous biopolymer within the cavity.

The flowable biopolymeric material is most preferably a liquid mixture liquid mixture comprised of human or animal-derived protein material and a di- or polyaldehyde. When introduced into the cavity of the tissue member, therefore, the liquid mixture may then react to form a cross-linked biopolymer in situ within the cavity thereby forming a bioprosthetic device therein. The liquid mixture may be formed in advance of being introduced into the cavity, or may be formed simultaneously during introduction into the cavity.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawing FIGURE which schematically depicts a portion of a patient's vertebral column showing a vertebral disc bioprosthetic in accordance with the present invention interposed between adjacent vertebrae.

DETAILED DESCRIPTION OF THE INVENTION

As used herein and in the accompanying claims, the term "bioprosthetic device" and like terns mean a combination comprised of a biological tissue member and a proteinaceous biopolymer which is chemically bound (linked) to the tissue of the tissue member.

The accompanying drawing FIGURE shows a segment of a patient's vertebral column VC wherein vertebral disc bioprosthetics 10 in accordance with the present invention are interposed between adjacent ones of the individual vertebrae V. The vertebral disc bioprosthetics 10 essentially include the fibrillar outer annulus 10-1 of the patient's natural vertebral disc following removal of the gelatinous core. The fibrillar outer annulus 10-1 thus bounds and defines an inner cavity into which a proteinaceous biopolymer 10-2 is injected in situ. The proteinaceous biopolymer (usually referred to hereinafter more simply as the "biopolymer") 10-2 thus fills completely the void space left following removal of the natural gelatinous core of the patient's natural vertebral disc. The biopolymer 10-2 thus acts as a shock-absorber of sorts similar to the natural functions attributable to the removed gelatinous core.

Virtually any suitable proteinaceous biopolymer may be employed in the practice of the present invention. In this regard, the term "proteinaceous biopolymer" and like terms mean a polymeric or copolymeric material which contains one or more units in the polymer chain comprised of natural, synthetic or sequence-modified proteins or polypeptides, and mixtures and blends of such polymeric and/or copolymeric materials.

One especially preferred biopolymer 10-2 that may be employed in the practice of this invention is a cross-linked reaction product of a two part mixture initially comprised of:

Part A: a water-soluble proteinaceous material of about 27-53% by weight of the mixture, and Part B: di- or polyaldehydes present in a weight ratio of one part by weight to every 20-60 parts of protein present by weight in the mixture and water, optionally containing non-essential ingredients to make up the balance of the composition.

Part A of the mixture is most preferably substantially an aqueous solution of a proteinaceous material of human or animal origin. Albumins including ovalbumins are preferred proteins, and serum albumins of human or animal origin are particularly preferred. The proteinaceous material may be a purified protein or a mixture in which the proteins such as serum albumins are the predominant ingredients. For example, the solid mixtures obtained by dehydration of blood plasma or serum, or of commercial solutions of stabilized plasma proteins, can be used to prepare Part A. These mixtures, generally referred to as plasma solids or serum solids, are known to contain albumins as their major ingredients, of the order of 50-90%. As used herein, the term "plasma" refers to whole blood from which the corpuscles have been removed by centrifugation. The term "serum" refers to plasma which has additionally been treated to prevent agglutination by removal of its fibrinogen and/or fibrin, or by inhibiting the fibrin clot formation through addition of reagents, such as citrate or EDTA. The proteinaceous material may also contain an effective amount of hemoglobin.

Part B is substantially an aqueous solution of di- or polyaldehydes. A wide range of these substances exist, and their usefulness is restricted largely by availability and by their solubility in water. For example, aqueous glyoxal (ethandial) is useful, as is aqueous glutaraldehyde (pentandial). Water soluble mixtures of di- and polyaldehydes prepared by oxidative cleavage of appropriate carbohydrates with periodate, ozone or the like are also useful. Glutaraldehyde is the preferred dialdehyde ingredient of Part B. When Parts A and B are brought together, the resultant product rapidly hardens to a strong, flexible, leathery or rubbery material within a short time of mixing, generally on the order of 15-30 seconds. The most preferred material for use in the present invention is commercially available from CryoLife, Inc. of Kennesaw, Ga. under the registered trademark "BIOGLUE". (See also, U.S. Pat. No. 5,385,606, the entire content of which is expressly incorporated hereinto by reference.)

The two components A and B noted above are either premixed and then applied, or simultaneously mixed and delivered through an in-line mixing/dispensing tip during the filling of the tissue-defined cavity. Upon reaction of the two components, the resulting biomaterial is a hydrogel that adheres to the surrounding tissue, intercalates into the voids of the surrounding tissues, is space filling, and is mechanically and biologically stable for some time. The material may be solid or sponge-like in appearance. Furthermore, it may contain organic or inorganic salts or other particulate matter to modify the physical properties of the resulting bioprosthetic device. Preferably, the biopolymer 10-2 will exhibit compressive strengths of at least 300 kPa (preferably between about 300 to about 600 kPa) and compressive moduli of 2.5 MPa, and creep moduli of 1.0 MPa. The ultimate compressive strength of the biopolymer 10-2 can be adjusted by altering the composition of the protein and cross-linker components and/or through the addition of various fillers.

As noted previously, the proteinaceous biopolymer that may be employed in the practice of the present invention may be include as on reactable component a natural, synthetic or sequence-modified (i.e., so-called "engineered") polypeptides (e.g., as disclosed more fully in U.S. Pat. Nos. 6,018,030; 5,374,431; 5,606,019; or 5,817,303, incorporated fully by reference herein). Thus, although many of the following examples employ albumin, it will be understood by those in this art that other reactable components may be employed satisfactorily. Reactable synthetic polymeric components, namely, those which contain functional groups to cause cross-linking (e.g. polyethylene-glycol polymers derivatized with electrophilic and nucleophilic groups such as amine, succinimidyl, anhydride, thiol) may also be employed in the practice of the present invention. See in this regard, U.S. Pat. Nos. 6,166,130; 6,051,648; or 5,900,245, the entirety of each being expressly incorporated hereinto by reference.

Nominal compressive mechanical properties that are obtained are similar to those of vertebral discs and lumbar vertebra. The compressive properties of the described biomaterial 10-2 are very different from highly rigid materials traditionally used as implantable structural elements such as stainless steel, titanium, polyacrylate bone cements, ceramics or carbon fiber composites, and hence allow for better biomechanical compatibility in selected indications. For example, the bioprosthetic vertebral discs of the present invention exhibit flexibility comparable to the biologically natural vertebral disc. More specifically, the bioprosthetic vertebral discs of the present invention exhibit flexibility comparable to the biologically natural vertebral disc after being subjected to at least about 5 million cycles of a cyclic load of about 0.85 MPa.

The particular properties of the biopolymer 10-2 can be "engineered" to suit specific end uses. For example, the biopolymer may include fibrous or particulate reinforcement ("filler") material, provided it is biocompatible.

Thus, natural or synthetic fibers, such as polyesters, nylons, polyolefins, glass and the like of virtually any desired denier may be employed. Furthermore, the reinforcing fibers may be used in the form of a continuous length of single fibers (i.e., monofilaments) or a yarn, roving or rope of multiple filaments. Moreover, the reinforcing media may be in the form of staple fibers of predetermined lengths which are spun into yarns, rovings and/or ropes of desired denier and continuous length. The mono- or multifilamentary reinforcing materials may also be in the form of woven or non-woven fabric structures. Suffice it to say here, that virtually any physical form of fibrous reinforcing material may be satisfactorily employed in the practice of the present invention.

The reinforcing material may also be in the form of particulates, such as synthetic or natural organic and inorganic particulate reinforcement materials. Some representative examples of such particulates include calcium carbonate, calcium phosphate, hydroxyapatite bone chips, ceramic particles and the like.

The present invention will be further described with reference to the following non-limiting Examples.

EXAMPLES

Example 1

A formulation formed of a protein solution (serum albumin) and a cross linker (gluteraldehyde) was contained in the separate chambers of a delivery device. When the device is triggered, the two components are expelled from their respective chambers into a mixing tip that combines the two solutions and mixes them as they travel over the static mixing elements present in the tip. A medical needle was attached to the mixing tip and the formulation injected into the distal space between the vertebra of an explanted pig spine. The tip can be attached to a needle, catheter, or other hollow tubular device for delivery, for example. After 30 seconds, the needle was withdrawn from the injection site. The material that was injected had polymerized in place and did not exude out of the needle hole. After 2 minutes, the disc-vertebra plate was dissected and the presence of the biomaterial seen.

Example 2

Bovine calf spines were obtained from a commercial slaughterhouse and cleaned by blunt and sharp dissection to expose the vertebral bodies and the discs. A 4 mm hole was made into the anterior face of the disc and the drill bit allowed to enter to the center of the nucleus. The nuclear material was removed using surgical forceps and curettes. The hollow space was filled with the formulation described in Example 1. The material that was injected polymerized in place and did not exude out of the hole. After 2 minutes the disc-vertebra plate was dissected and the presence of the biomaterial seen.

Example 3

Bovine calf spines were obtained from a commercial slaughterhouse and cleaned by blunt and sharp dissection to expose the vertebral bodies and the discs. The top and bottom of the vertebral bodies were cut parallel to each other at mid-height using a miter box to yield a bone/disc/bone motion segment. A 4 mm hole was made into the anterior face of the disc and the drill bit allowed to enter into the center of the nucleus. The nuclear material was removed using surgical forceps and curettes. The hollow space was filled with the formulation described in Example 1. The material that was injected had polymerized in place and did not exude out of the hole.

Once polymerization had occurred, the construct could be compressed by hand in the front-back and left-right axes, indicating flexibility was retained after repair of this segment. Then, the construct was placed in a biomaterials testing device (instron electromechanical test station) and compressed repeatedly to a load of 700 N to condition the construct. Thereafter, a constant load of 700 N was applied to measure compressive creep. The load was held for 10 min. During this time, the polymerized material did not exit from the distal space or the hole. A force of 700 N is the published literature value for the load a lumbar spinal disc experiences when a person of average built is standing upright. The experiment was repeated on 5 separate samples.

In this example, the motion segment height was measured before removal of the nucleus, after removal of the nucleus, after filling with the biomaterial, and after loading and releasing the load. It was found that (1) the removal of the nucleus reduced the overall height of the material, as well as the compressibility, (2) the filling with the biomaterial restored the disc height and the compressibility.

Example 4

A disc of biomaterial formed by injecting a volume of material with the formulation described in Example 1 into a cavity mold was compressed for 100 and 1000 cycles at a compression rate of 100 mm/min between a minimum stress of 200 kPa and a maximum stress of either 470 or 800 kPa (equivalent to a normal lumbar disc, cross sectional area of 1500 mm$^2$, loaded between 300 N and 700 or 1200 N). The disc element did not exhibit fracture, permanent deformation, or demonstrate a loss of hydration (by mass loss analysis). A force of 1200 N is the published literature value for the compressive load a lumbar spinal disc experiences when a person of average built flexes forward.

Example 5

Bovine calf spines were obtained and prepared as described in Example 3. In this example, the nucleus pulposus was accessed either from an anterior or a posterolateral direction. The constructs were then placed under a cyclic load of 0.85 MPa at 5 Hz and the load applied for >5 million cycles. During this time, the constructs were kept in physiological saline solution containing a non-fixative biocidal agent. At the end of the test period, the constructs were removed and the disc sliced parallel to the end plates to observe the status of the implants. The implant present in the cavity created by the removal of the nucleus pulposus, was intact and flexible.

Example 6

Samples of the biomaterial were formed as described in Example 4. The biomaterial was then placed under a cyclic load of 0.5 MPa at approximately 2 Hz and the load applied for either >5 million cycles or >10 million cycles. During this time, the constructs were kept in physiological saline solution containing a non-fixative biocidal agent. The test samples remained intact throughout the duration of the test, and demonstrated <10% loss in original height.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for the in situ formation of a bioprosthetic core for a vertebral disc comprising:
    substantially filling a cavity of the vertebral disc defined by a surrounding biological tissue material with a flowable material which comprises:
        a first reactable component consisting of a human or animal derived protein material and a second reactable component consisting of a di- or polyaldehyde material, and/or
        reaction products of the first reactable component and the second reactable component; and
    allowing the first reactable component and second reactable component or their reaction products to at least partly solidify within the biological tissue material and chemically bind to the surrounding biological tissue material, thereby forming the bioprosthetic core, the bioprosthetic core being load distributing and compressible without exhibiting substantial permanent deformation.

2. The method of claim 1, which comprises injecting the flowable material into the cavity.

3. The method of claim 2, wherein the first reactable component and the second reactable component are combined and mixed simultaneously while being injected into the cavity.

4. The method of claim 2, wherein the first reactable component and the second reactable component are premixed before being injected into the cavity.

5. The method of claim 1, further comprising providing a fibrous or particulate filler material in the flowable material.

6. The method of claim 1, wherein the protein material comprises bovine or human serum albumin or hemoglobin.

7. The method of claim 1, wherein the di- or polyaldehyde comprises glutaraldehyde.

8. The method of claim 1, wherein the di- or polyaldehyde is present in a weight ratio of one part by weight to every 20-60 parts of protein present by weight prior to reacting with the first reactable component.

9. A method for the formation of a bioprosthetic core for a vertebral disc comprising:
    (a) providing a vertebral disc having a fibrillar outer annulus which surrounds and defines an interior cavity formed by removal of a natural gelatinous core material therefrom;
    (b) substantially filling the cavity with a flowable material which comprises a first reactable component consisting of a human or animal derived protein material and a second reactable component consisting of a di- or polyaldehyde material, and/or reaction products of the first reactable component and the second reactable component; and
    (c) reacting the first and second reactable components so that the flowable material at least partly solidifies in situ within the cavity and chemically binds to the surrounding biological tissue of the cavity thereby forming the bioprosthetic core, the vertebral disc having the bioprosthetic core therein exhibiting flexibility comparable to a biologically natural vertebral disc.

10. The method of claim 9, which comprises injecting the first and second reactable components in situ within the cavity, and allowing the first and second reactable components to at least partly solidify by reaction therein.

11. The method of claim 10, wherein the first reactable component and the second reactable component are combined and mixed simultaneously while being injected into the cavity.

12. The method of claim 10, wherein the first reactable component and the second reactable component are premixed before being injected into the cavity.

13. The method of claim 9, further comprising providing a fibrous or particulate filler material in the flowable material.

14. The method of claim 9, wherein the protein material comprises bovine or human serum albumin or hemoglobin.

15. The method of claim 9, wherein the di- or polyaldehyde comprises glutaraldehyde.

16. The method of claim 9, wherein the di- or polyaldehyde is present in a weight ratio of one part by weight to every 20-60 parts of protein present by weight prior to reacting with the first reactable component.

17. A method for the formation of a bioprosthetic core for a vertebral disc comprising:

(a) providing a vertebral disc having a fibrillar outer annulus which surrounds and defines an interior cavity formed by removal of a natural gelatinous core material therefrom;

(b) substantially filling the cavity with a flowable material which comprises a first reactable component consisting of a human or animal derived protein material and a second reactable component consisting of a di- or polyaldehyde material, and/or reaction products of the first reactable component and the second reactable component; and (c) reacting the first and second reactable components so that the flowable material at least partly solidifies in situ within the cavity and chemically binds to the surrounding biological tissue of the cavity thereby forming the bioprosthetic core, the bioprosthetic core being capable of withstanding compression for 100 and 1000 cycles at a compression rate of 100 mm/min between a minimum stress of 200 kPa and a maximum stress of 800 kPa without exhibiting permanent deformation and loss of hydration.

18. The method of claim 17, which comprises injecting the first and second reactable components in situ within the cavity, and allowing the first and second reactable components to at least partly solidify by reaction therein.

19. The method of claim 18, wherein the first reactable component and the second reactable component are combined and mixed simultaneously while being injected into the cavity.

20. The method of claim 18, wherein the first reactable component and the second reactable component are premixed before being injected into the cavity.

21. The method of claim 17, further comprising providing a fibrous or particulate filler material in the flowable material.

22. The method of claim 17, wherein the protein material comprises bovine or human serum albumin or hemoglobin.

23. The method of claim 17, wherein the di- or polyaldehyde comprises glutaraldehyde.

24. The method of claim 17, wherein the di- or polyaldehyde is present in a weight ratio of one part by weight to every 20-60 parts of protein present by weight prior to reacting with the first reactable component.

* * * * *